(12) United States Patent
Oboh et al.

(10) Patent No.: US 8,939,989 B2
(45) Date of Patent: Jan. 27, 2015

(54) OBSTETRIC FORCEPS

(76) Inventors: Alex Oboh, Hull (GB); Timothy Flood, Harrogate (GB); Richard Hall, Harrogate (GB); Paul Thorning, Bradford (GB)

(\*) Notice: Subject to any disclaimer, the term of this patent is extended or adjusted under 35 U.S.C. 154(b) by 0 days.

(21) Appl. No.: 13/641,976

(22) PCT Filed: Apr. 20, 2011

(86) PCT No.: PCT/GB2011/050790
§ 371 (c)(1),
(2), (4) Date: Apr. 30, 2013

(87) PCT Pub. No.: WO2011/131988
PCT Pub. Date: Oct. 27, 2011

(65) Prior Publication Data
US 2013/0211417 A1 Aug. 15, 2013

(30) Foreign Application Priority Data
Apr. 20, 2010 (GB) .................................. 1006570.4

(51) Int. Cl.
*A61B 17/42* (2006.01)
*A61B 17/44* (2006.01)
*A61B 19/00* (2006.01)

(52) U.S. Cl.
CPC ............ *A61B 17/44* (2013.01); *A61B 2017/445* (2013.01); *A61B 2017/447* (2013.01); *A61B 2019/444* (2013.01); *A61B 2019/464* (2013.01)
USPC ....................................................... 606/119

(58) Field of Classification Search
CPC .... A61B 17/29; A61B 17/44; A61B 17/2909; A61B 2017/44; A61B 2017/445; A61B 2017/447; A61B 2017/291; A61B 2017/2911; A61B 2017/2912; A61B 2017/2913; A61B 2017/2915; A61B 2017/2916; A61B 2017/2917; A61B 2017/2918; A61B 2017/2919; A61B 2017/292; A61B 2017/2922; A61B 2017/2923; A61B 2017/2924; A61B 2019/444; A61B 2019/464
USPC ............. 606/1, 119, 122, 205, 206, 207, 208, 606/121, 123, 124; 600/587, 591
See application file for complete search history.

(56) References Cited

U.S. PATENT DOCUMENTS 657,203 A \* 9/1900 Neumeier, Jr. ................ 606/124
820,845 A 5/1906 Barton
(Continued)

FOREIGN PATENT DOCUMENTS

DE 4235442 A1 4/1994
FR 2761875 10/1998
(Continued)

OTHER PUBLICATIONS

International Search Report and Written Opinion for PCT/GB2011/050790, dated Oct. 25, 2011.
(Continued)

*Primary Examiner* — Melanie Tyson
*Assistant Examiner* — Christian Knauss
(74) *Attorney, Agent, or Firm* — Squire Patten Boggs (US) LLP

(57) ABSTRACT

A pair of obstetric forceps is described. The forceps comprise a pair of blades for holding the head of a baby and a handle having at least one part by which a user can apply a pulling force on the head of the baby in use. A mechanically operated force indicator is connected to the at least one part of the handle and is operable to provide a visual indication of the amount of pulling force being applied to the head of the baby when a user applies a pulling force on the head of the baby in use. A mechanically operated disabling device is operable to at least partially disable the obstetric forceps when a maximum pulling force has been exceeded. The blades can each have a superior rim and inferior rim wherein the greatest separation between the superior rims is greater than the greatest separation between the inferior rims when the obstetric forceps are in a closed configuration so that the blades adopt the form of an at least partially bowl shape.

15 Claims, 9 Drawing Sheets

(56) References Cited

U.S. PATENT DOCUMENTS

| | | | |
|---|---|---|---|
| 1,116,099 A * | 11/1914 | Morse | 606/124 |
| 1,672,570 A * | 6/1928 | La Breck | 606/122 |
| 1,760,720 A * | 5/1930 | Roderick | 606/124 |
| 2,224,318 A | 12/1940 | Schoenbechler | |
| 2,293,984 A * | 8/1942 | Kirschbaum | 606/124 |
| 2,637,320 A * | 5/1953 | Greenberg | 606/122 |
| 3,384,088 A * | 5/1968 | Miseo | 606/121 |
| 3,605,748 A * | 9/1971 | Salinas-Benavides | 606/124 |
| 3,665,925 A * | 5/1972 | Dersookian | 606/124 |
| 3,785,381 A * | 1/1974 | Lower et al. | 606/122 |
| 3,789,849 A * | 2/1974 | Laufe et al. | 606/122 |
| 4,151,846 A * | 5/1979 | von Zeppelin et al. | 606/122 |
| 4,248,233 A * | 2/1981 | von Zeppelin et al. | 606/122 |
| 4,815,476 A * | 3/1989 | Clossick | 600/564 |
| 5,047,046 A * | 9/1991 | Bodoia | 606/205 |
| 5,139,503 A * | 8/1992 | Salas-Ceniceros | 606/122 |
| 5,308,357 A * | 5/1994 | Lichtman | 606/205 |
| 5,578,043 A * | 11/1996 | Galstian | 606/119 |
| 5,638,827 A * | 6/1997 | Palmer et al. | 600/564 |
| 5,649,934 A | 7/1997 | Smeltzer, III et al. | |
| 5,674,243 A * | 10/1997 | Hale | 606/205 |
| 5,849,017 A * | 12/1998 | Reynolds et al. | 606/122 |
| 5,893,878 A * | 4/1999 | Pierce | 606/207 |
| 5,997,545 A * | 12/1999 | Doherty et al. | 606/102 |
| 6,425,899 B1* | 7/2002 | Biehl | 606/122 |
| 6,638,209 B2* | 10/2003 | Landgrebe | 600/30 |
| 7,014,642 B1* | 3/2006 | Perone | 606/122 |
| 7,291,156 B1* | 11/2007 | Perone | 606/122 |
| 2003/0220655 A1* | 11/2003 | Rose | 606/122 |
| 2009/0204124 A1 | 8/2009 | Ross | |
| 2011/0245865 A1* | 10/2011 | Harper et al. | 606/205 |

FOREIGN PATENT DOCUMENTS

| | | |
|---|---|---|
| GB | 382243 A | 10/1932 |
| WO | WO 98/11835 | 3/1998 |

OTHER PUBLICATIONS

Search Report for UK Application No. GB1006570.4, dated Jul. 30, 2010.

* cited by examiner

OBSTETRIC FORCEPS

BACKGROUND

1. Field of the Invention

The present invention relates to obstetric forceps. In particular, the invention relates to obstetric forceps which provide feed back to a user when excessive force is applied to a baby's head. The invention also relates to obstetric forceps with improved blades.

2. Description of Related Art

Obstetric forceps for assisting in the birth of a baby are well known. In practice, the amount of pulling force which is applied to a baby during use of the forceps depends on a number of factors. Some of these factors relate to the mother and baby and other relate to the user of the forceps. For example, the user's experience, levels of tiredness and physical size and strength may all affect how much force is applied to the baby while trying to deliver the baby using forceps. If too much force is applied then the baby or mother or both can be harmed in a variety of ways. Alternatively, if a user does not apply enough force, then the use of forceps can be abandoned prematurely in favour of other potentially more invasive or harmful delivery techniques.

Systems that monitor the amount of pulling force applied in use while using obstetric forceps are known. Examples of such systems are described in, for example, U.S. Pat. Nos. 7,163,544, 7,014,642 and 5,649,934. However, all of these systems involve electronic equipment to monitor the force and provide an indication of the applied pulling force via a computer. Such systems are complex to use, set up and install, costly and add significantly to the equipment present in a delivery room.

Obstetric forceps are also known in which the amount of pulling force is measured with mechanical devices. Such systems are described, for example, in U.S. Pat. Nos. 3,785,381, 3,665,925, U.S. 2003/0220655 and U.S. Pat. No. 3,789,849. Such forceps provide limited feedback to a user as to how much force is being applied to a baby in use.

Therefore, it would be advantageous to provide obstetric forceps providing improved user feedback of the force being applied to the baby by the forceps in use.

Further, irrespective of the amount of force applied, it is also possible for forceps to harm the mother and/or baby. This is particularly the case where parts of the forceps engage the skin or soft tissue of the mother and/or baby.

Therefore, additionally or alternatively, it would be advantageous to provide obstetric forceps providing reduced harm to the mother and/or baby in use.

BRIEF SUMMARY

A first aspect of the invention provides a pair of obstetric forceps. The forceps can comprise a pair of blades at a first end for holding the head of a baby and a handle at a second end. The handle can include at least one part by which a user can apply a pulling force on the head of the baby in use. A mechanically operated force indicator can be connected to the at least one part of the handle and is operable to provide a visual indication of the amount of pulling force being applied to the head of the baby when a user applies a pulling force on the head of the baby in use. The forceps can also include a mechanically operated disabling device operable to at least partially disable the obstetric forceps when a maximum pulling force has been exceeded.

The disabling device at least partially disables the forceps if a user applies a force greater than a predetermined maximum safe pulling force so that the forceps are no longer in their normal use state. Hence, by at least partially disabling the forceps a user immediately becomes aware that they have reached the maximum safe pulling force and so may consider using an alternative technique to deliver the baby. Also, a user can be confident to keep using the forceps and applying a greater pulling force if the forceps are still in the normal use state and so may avoid using a more interventional technique to deliver the baby.

It can be preferable to only partially disable the forceps as in some circumstances, e.g. an emergency, it may be helpful to still be able to use the forceps to apply a greater force so as to deliver the baby. However, the benefit of the invention of providing an immediate tactile feedback to the user, and also an effect noticeable by other people present at the delivery, that the maximum safe force has been reached is still provided by partially disabling the forceps.

The force indicator also provides a real time indication of the force being applied and so also assists the user in the safe use of the forceps. For example the user might view the force indicator to see how much more force might be applied before the forceps are disabled.

Further, the forceps are entirely mechanical and are a self contained device and therefore are easy to use, do not need setting up and do not take up more space than conventional forceps.

Various parts of the forceps may be partially or wholly disabled when the predetermined maximum force is exceeded. For example, the disabling device may at least partially or wholly disable the at least one part when the maximum force is exceeded. The at least one part may be a part of the handle, such as a finger grip or grips, or the handle itself or any part of the forceps commonly held by a user to exert a pulling force in use. A part of the blades or shanks attaching the blades to the handled may be partially or wholly disabled by the disabling device.

The maximum pulling force may be approximately 135N, 120N or 115N.

The disabling device can at least partially disable the entire handle when the maximum force is exceeded. Partially disabling the handle provides instant tactile feedback to the user that the safe force has been exceeded, but allows the handle still to be used if necessary, e.g. in an emergency, to deliver a baby.

The handle or part can be wholly or partially disabled by changing various properties of the handle or part. For example, the position of the handle or part can be changed, the resilience of the handle or part can be changed, the handle or part can become loose or slack or adopt a different configuration when wholly or partially disabled.

The disabling device can include a detachable coupling between the at least one part or the handle and the blades. The detachable coupling can be directly or indirectly attached to the part or handle and the blades. The detachable coupling can detach when the predetermined maximum force is exceeded.

The detachable coupling can include a resilient member which resiliently biases the at least one part or handle in a first position relative to the blades. The first position can be toward the blades of the forceps. When the detachable coupling detaches the at least one part or handle can be no longer biased toward the first position. The at least one part or handle can become free to move relative to the remainder of the forceps. The at least one part or handle can slide freely relative to the remainder of the forceps when the detachable coupling detaches.

The pair of obstetric forceps can further comprise a restraint which prevents the part or handle entirely separating from the forceps when the obstetric forceps become at least partially disabled. This allows the part or handle still to be used, although in an altered state, after the partial disablement of the forceps.

The part or handle can entirely separate from the forceps when the obstetric forceps become disabled. This prevents a handle or the part being available to a user to pull on the forceps after the maximum force has been exceeded.

The force indicator can be responsive to an increase in pulling force only. The force indicator can include a movable component and a driving component which drives the movable component to indicate the force being applied. The movable component may be a slidable component or a rotatable component. The driving component may be a camming component and the movable component may include a camming surface against which the camming component acts to alter the position of the movable component. The force indicator may include a plurality of visible indicia corresponding to different force levels. The visible indicia can include, letters, numbers, symbols, characters, colours or any combination thereof. Preferably the visible indicia comprises a plurality of colours and more preferably at least three colours. The three colours may be red, amber and green.

Preferably the force indicator automatically records a maximum pulling force applied. Hence, after use of the forceps the force indicator can be read to determine the maximum force applied during use. The force indicator can 'latch' at the maximum pulling force that has been applied during use of the forceps. The force indicator can be re-settable so when the forceps are intended to be re-used in a subsequent delivery.

The obstetric forceps can comprise two parts. Each part can have a shank part attached to a respective blade. The shanks can be pivotably connectable to each other by a releasable pivot mechanism to form a scissors-like construction. Each shank can provide a respective interacting formation of the pivot mechanism. The pivot mechanism can be in the form of a pin and socket joint.

A first of the shanks can be releasably fastened to the handle by a locking mechanism. A second of the shanks can be permanently attached to the handle. The locking mechanism can be operable by rotation. The locking mechanism can include a rotatable part of the handle which acts to capture at least a portion of the first shank within the handle.

A second aspect of the invention provides a pair of obstetric forceps. The forceps can include a pair of blades for holding the head of a baby and a handle by which a user can apply a pulling force on the head of the baby via the blades in use. The blades can be configured and shaped so as to adopt the form of at least part of a bowl shape so as to cup the baby's head when the forceps are closed about the baby's head in use. Each blade can have a superior rim and inferior rim. The greatest separation between the superior rims of can be greater than the greatest separation between the inferior rims of the blades.

By tilting the blades of the forceps to form a bowl like shape, the baby's head can be cupped in and supported by the blades more than conventional blade shapes which tend to engage predominantly the side of the baby's head. Also, by tilting the blades of the forceps away from the straight up-down orientation the rims of the forceps present a smoother shaped surface, less like a edge, to the vaginal wall and so help reduce potential damage to the vaginal wall, such as cuts or abrasion, during delivery of the baby, A cephalic face of the superior and/or inferior rims can include one or more grip formations for increasing or enhancing the grip on a baby's head. The grip formations may be raised formations.

The blades can be made from a first material and the grip formations can be made from a second material which is softer than the first material. The softer material helps to increase grip while reducing potential marking or harm to the baby's head and/or face. The second material can be a polymer.

A vaginal wall contacting surface of the inferior rim and/or the superior rim can includes a plurality of formations which reduce the surface area of the contacting surface presented by the blades. The formations can be raised formations or recesses. The formations can by generally triangular or pyramidal shaped. The formations can be rib or trough shapes.

A vaginal wall contacting surface of the superior and/or inferior rim of each blade can presents a smoothly curved surface to reduce the risk of harm to the vaginal wall. The surface can have a continuous curve and no edge like discontinuities.

Preferred features of the second aspect of the invention can also be preferred features of the first aspect of the invention and vice versa.

A further aspect of the invention provides a method of using a pair of obstetric forceps during delivery of a baby. The method may comprise locating blades of the forceps about the head of the baby. A user then pulls on a handle or part of a handle of the forceps to apply a force to the head of the baby. The handle or part of the handle becomes at least partially disabled when the force applied is greater than a predetermined maximum force.

The method may alternatively or additionally include cupping the blades of the forceps about the head of the baby.

The method may further include assembling two parts of the forceps while the blades engage the head of the baby by assembling a pivot mechanism of the forceps.

The method may further include locking a first shank of the forceps to the handle of the forceps to lock the blades in a closed configuration. Locking the shank may comprise rotating a handle part of the forceps to enclose the first shank within the handle.

The method may further comprise providing a visible indication of the maximum force that has currently been applied using the forceps.

BRIEF DESCRIPTION OF THE DRAWINGS

Embodiments of the invention will now be described in detail, and by way of example only, and with reference to the accompanying drawings, in which.

DETAILED DESCRIPTION

In the Figures, similar parts share common reference signs unless indicated otherwise. FIGS. 1 to 9 show a first embodiment of the obstetric forceps of the invention and FIGS. 10 to 13 show a second embodiment of the obstetric forceps of the invention. The second embodiment is substantially similar to the first embodiment, but with some structural differences, and operates and is used in a similar manner to the first embodiment. The reference signs used for the second embodiment are similarly numbered to the reference signs for the first embodiment but prefixed with one.

Figure 1:
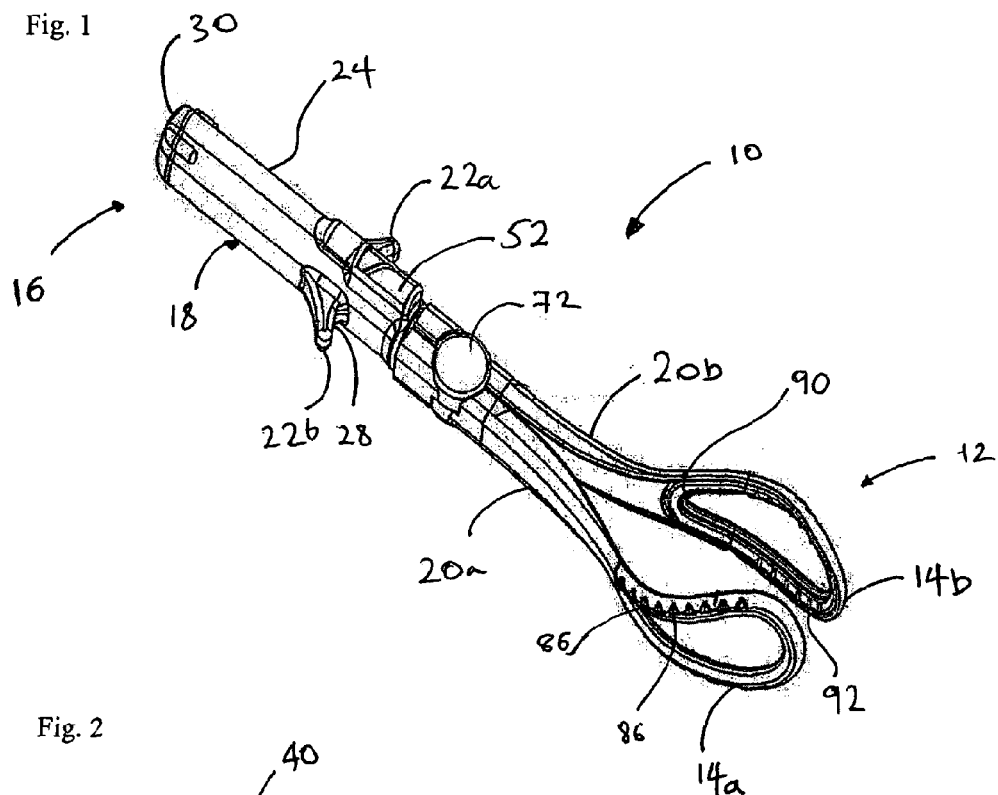
FIG. 1 is a perspective view of a pair of obstetric forceps according to the present invention.

With reference to FIG. 1 there is shown a pair of obstetric forceps 10 according to the invention. The obstetric forceps 10 have first and second blades 14a, 14b toward a first or distal end 12 and a handle 18 toward second or proximal end 16. The first and second blades 14a, 14b are connected to the handle 18 via respective first 20a and second 20b shanks. First and second finger grips 22a, 22b extend from opposite sides of the handle 18 such that a user of the obstetric forceps 10 can hook their fingers over the finger grips to help exert a pulling force on the head of a baby.

The obstetric forceps 10 include a mechanically operated force indicator which is operable in use to indicate the amount of pulling force which is being applied using the forceps by a user. The force indicator is entirely mechanically operated. The force indicator includes a force display component in the form of a barrel 52 which is rotatably mounted and is driven to rotate when the pulling force increases. The barrel 52 has differently coloured portions which are displayed sequentially as the barrel 52 is rotated. In the embodiment there are green, amber and red coloured portions which are each indicative of a pre-selected range of pulling force, with red indicating a pulling force close to a maximum pulling force which it is considered safe to apply using the forceps.

The mechanical force indicator advantageously provides an easily readable visual indication to a user of the pulling force currently being applied at any given time and also an approximate indication of the amount of further force which can be safely applied.

Further, the construction of the force indicator (as described below) is such that the force indicator records force increases only during use of the forceps, and so the maximum force applied during use of the forceps is automatically recorded by the force indicator and can be referred to or recorded for other purposes. For example, it may be desirable to have a record of the maximum applied force as part of the medical records, for clinical governance or as evidence of the maximum pulling force used for legal purposes.

Figure 3:
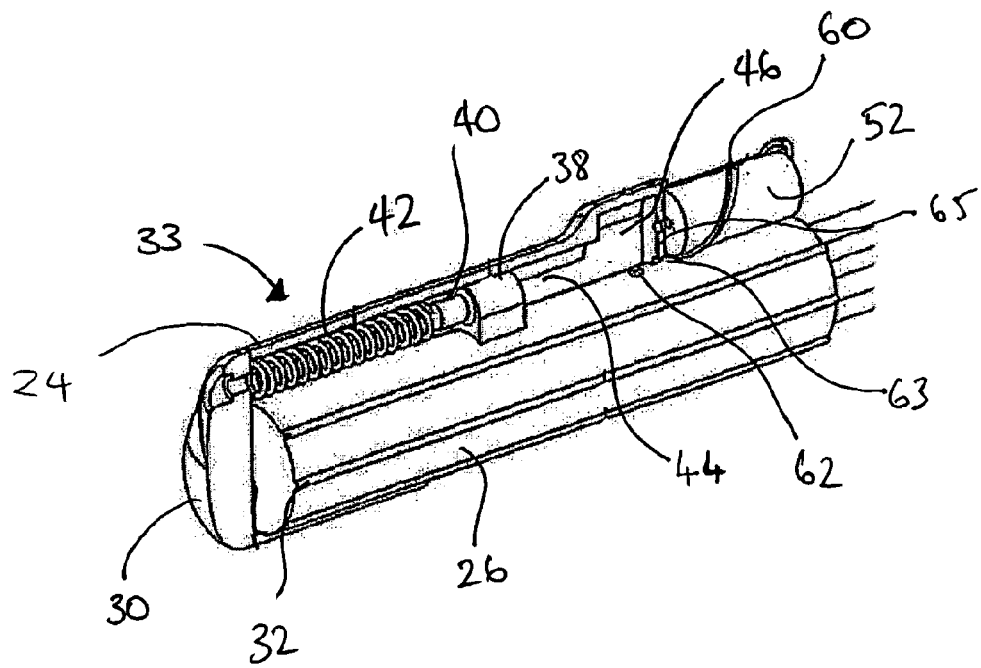
FIG. 3 shows parts of the handle portion of the obstetric forceps of FIG. 1 with a portion of the outer casing of the handle removed so as to reveal the disabling device.

The obstetric forceps 10 also include a mechanically operating disabling device as shown in FIG. 3. The disabling device operates to at least partially or wholly disable the handle or a part of the handle pulled by a user to prevent the forceps being used in the same way as they could be used prior to operation of the disabling device when a safe force limit has been reached. This provides immediate tactile feedback to a user that once a safe force limit has been reached, the user can no longer use the forceps in the original manner prior to their at least partial disablement.

The disabling device includes a detachable coupling 33 which partially disables the handle of the obstetric forceps after a predetermined amount of pulling force, i.e. the maximum safe force limit, has been reached. The detachable coupling 33 links an outer casing part 24 of the handle 18 which can move relative to the blades 14a, 14b when a pulling force is applied. The detachable coupling 33 incorporates a resilient element in the form of a spring 42 which provides a biasing force to the movement of the outer casing 24 relative to the blades 14a, 14b. The biasing force caused by spring 42 can be felt by a user exerting a pulling force as the handle casing slides generally along the longitudinal axis of the forceps and provides an indication that the obstetric forceps are working "normally", i.e. in the non-disabled state.

When the maximum pulling force has been exceeded, the spring 42 decouples the outer casing 24 which can then slide freely relative to the blades. This provides a user with immediate tactile feedback that the maximum force limit has been reached and the forceps 10 should not be used further. The casing part of the handle will simply slide along the forceps without exerting any pulling force and hence the handle of the forceps, although it can still be held, no longer operates in the same way as it did originally to allow a pulling force to be exerted and so has become at least partially disabled. In this way, the forceps 10 are considered to be partially disabled as the previous normal use of the forceps is no longer possible.

As can be seen in FIG. 3, the handle 18 includes a restraint to prevent the outer casing 24 becoming entirely separated from the rest of the obstetric forceps 10 when the disabling device operates and the spring 42 decouples. When a user is pulling on the handle, as the spring decouples and the biasing force is removed, the outer casing 24 of the handle 18 will undergo a sudden but short acceleration and deceleration due to the removal of the biasing force and a portion of the outer casing meeting the restraint. Hence, the decoupling provides a user with a tactile indication when the maximum force has been reached.

Figure 2:
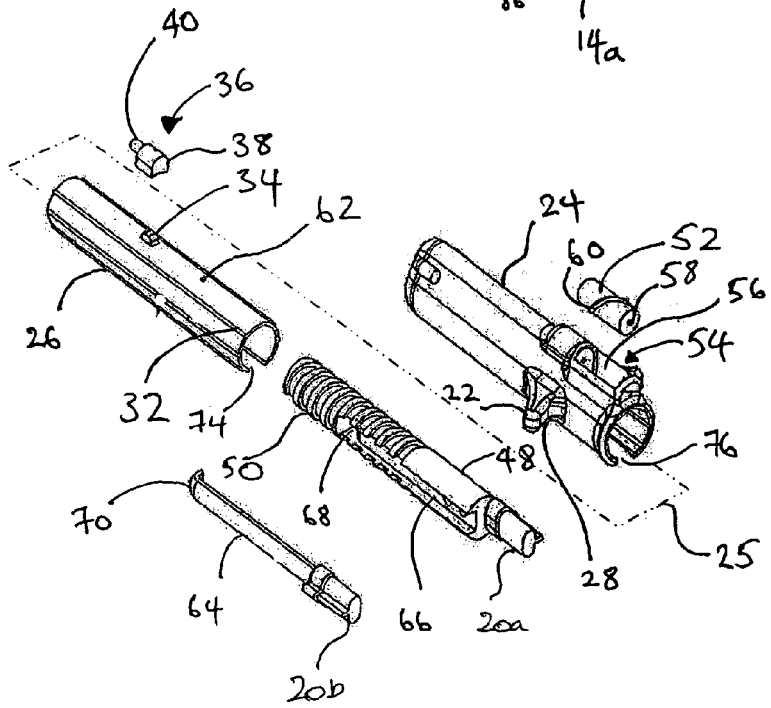
FIG. 2 is an exploded view of the handle portion of the obstetric forceps of FIG. 1.

FIG. 2 shows an exploded view of the obstetric forceps 10. The handle 18 includes an outer casing 24 in the form of an elongate cylinder which is sized to be received by the hand of a user. An inner or core member 26 of the handle is received within the outer casing 24 which can slide therealong and an anchor member 48 is received within the inner member 26 on a threaded portion 50. The first shank 20a extends from anchor member 48 and extends from a proximal end 12 of the handle 18. The outer casing 24, inner member 26 and anchor member 48 are assembled coaxially along the dashed axis 25 shown in FIG. 2. A free end portion 64 of the second shank having a hooked free end 70 can be received within elongate channel 66 in the anchor member 48 as described below.

The outer casing 24 includes pulling portions in the form of finger grips 22. The finger grips 22 are wing-like formations which extend and project from either side of the outer casing 24 in a common plane parallel to the longitudinal axis of the outer casing 24. The face of each finger grip 22 directed toward the blade end of the forceps includes a curved portion 28 around which a user can hook a finger or fingers, or otherwise hold to gain purchase, so as to exert a pulling force. The finger grips 22 are arranged such that when the handle 18 is grasped from above, the handle 18 is received in the palm of the user and a pulling force can be exerted on the finger grips 22 by hooking the fore and index fingers around the respective curved portions 28.

The outer casing 24 is open at one end 12 such that it can receive the inner or core member 26. The other end 16 of the outer casing 24 is closed by a removable cap 30. The removable cap 30 is secured with mechanical fasteners in the form of a pair of screws.

The inner member 26 is coaxially received within the outer casing 24 of the handle 18 such that a pulling force applied along the longitudinal axis of the forceps 10 via the finger grips 22 and/or handle when the blades 14a, 14b are anchored causes the outer casing 24 to slide relative to and along the inner member 26 in a direction away from the blades. A plurality of longitudinal ribs 32 are provided on the outer surface of the inner member 26. The ribs 32 engage with corresponding trough formations on the inner surface of the outer casing 24 so as to prevent rotational movement between the outer casing 24 and the inner member 26 whilst still allowing for relative longitudinal sliding movement.

The remaining parts shown in FIG. 2 are described in detail with reference to FIGS. 3 and 4 below.

FIG. 3 shows the detachable coupling 33 which connects the inner member 26 and outer casing 24. The detachable coupling mechanism 33 includes a two-part coupling comprising a male coupling part 34 and a female coupling part 36, and a resilient member in the form of a spring 42.

The male coupling part 34 is located on and stands proud of the uppermost surface of the inner member 26, as shown in FIG. 2, and is in the form of a cuboid formation having chamfered upper distal and proximal edges. The purpose of the chamfered portions is to allow a corresponding female coupling part 36 to separate from the male coupling part 34 more easily under a lateral separating force provided by the spring 42 when extended.

The female coupling part 36 includes a hollow body portion 38 which is mateably received on the male coupling part 34. The female coupling part 36 has a cylindrical projection 40 extending from a rearward face thereof and which is attached to a first end of the spring 42. A second end of the spring 42 is attached to the cap 30 of the outer casing 24. Hence, when the forceps 10 are assembled, the spring 42 biases the casing 24 along the longitudinal axis of the forceps and toward the blade end of the forceps as described above.

When assembled, the male 34 and female 36 coupling parts of the two part coupling are snugly received within a corresponding channel 44 located within an uppermost part of the outer casing 24. The dimensions of the channel 44 and the two part coupling are such that the coupling can slide along when a pulling force is exerted and the male and female parts are prevented from separating under the tensile force of the spring 42 by abutment of the roof of the channel 44 on top surface of the female part 36.

The channel 44 which receives the two part coupling opens out or has a greater height at a second end to form a chamber 46. The height of the chamber 46 is at least that of the separated height of the male coupling part 34 and female coupling part 36 in addition such that the female coupling part can ride up and pass freely over the male coupling part 34. When the two part coupling enters the chamber 46 in use, the spring 42 exerts a force on the female coupling part 36 due to the relative displacement between the outer casing 24 and the inner casing 26. The magnitude of the force and the dimensions of the two part coupling are such that the female part 36 can ride up over the chamfered proximal upper edge of the male part 34 into the chamber 46 and retracts back down the channel 44. In this way, the detachable coupling 33 disconnects the inner core and handle and thereby partially disables the forceps 10.

The biasing force provided by the spring 42 can be felt by a user exerting a pulling force so as to provide an indication that the forceps 10 are operating normally. When a maximum force limit (as set by the strength of the spring and the positioning of the couple mechanism and chamber) has been reached and the detachable coupling 33 has disconnected, the outer casing 24 is no longer biased toward the blade end of the forceps and will slide freely relative to the inner core. Thus, if a user were to continue applying a pulling force they would experience no resistance to the relative sliding motion between the outer casing 24 and the inner member 26 and the user would know that the maximum pulling force has been exceeded by the obstetric forceps 10 and that they should not be used.

The anchor member 48 is in the form of an elongate cylinder having proximal and distal end faces. A distal portion of the outer cylindrical anchor member 48 includes a threaded portion 50 which is received within a corresponding threaded portion on the inside of the hollow cylinder of the inner member 26. When screwed together, the respective threaded portions engage so as to prevent separation of the inner and anchor members The blade shanks 20a, 20b are connected to the handle 18 via the anchor member 48. The first shank 20a is permanently connected to the anchor member 48 and extends from an end face thereof, parallel to the longitudinal axis of the outer casing 24. The second shank 20b includes a free end 64 having a hooked end 70 which is received and retained in the handle via a locking mechanism as described below with reference to FIG. 4. When the second shank 20b is retained within the locking mechanism it extends from the proximal face of the anchor member 48 parallel to the first shank 20a such that the first and second blades 14a, 14b are equidistantly and symmetrically spaced in relation to the longitudinal axis of the outer casing 24.

The rotatable barrel 52 is located in a housing 54 which is provided on the upper surface of the outer casing 24. The housing 54 includes a window 56 portion through which a portion of the barrel 52 can be viewed by a user when the forceps 10 are in use. The barrel 52 includes a pair of projections 58 coaxially mounted on respective ends thereof which are received by corresponding sockets located within proximal and distal walls of the housing 54. The projections and sockets cooperate to act as bearings on which the barrel 52 can rotate about its longitudinal axis.

The barrel 52 includes a helical rib 60 on its outer surface, the rib having a pitch such that it extends once around the barrel and along the length of the barrel. The rib can engage in use with a driving or camming member 62 located on the upper side of the inner member 26. When the inner member 26 slides relative to the outer casing 24 upon application of a pulling force, the driving member 62 passes freely through a notch in the end wall 65 of the barrel housing 54 and contacts the helical rib 60 causing the barrel 52 to rotate.

The outer surface of the barrel 52 is segmented into three angularly separated portions each of a different colour indicating a range of applied pulling force. As the barrel 52 is rotated the individual coloured portions, which in the present embodiment are green, amber and red, are sequentially presented at the window portion 56 in turn as the force increases so as to provide a visual indication of the pulling force which is currently being applied by the user.

It will be appreciated that the dimensions of the barrel 52 and inner member 26 and the strength of spring 42 will all affect the range of force which is indicated by each coloured portion. In the described embodiment, a first, green coloured portion corresponds to a range of force of approximately 0 to 75N, a second, amber coloured portion corresponds to a pulling force in the approximate range 75N to 105N and a third, red coloured portion corresponds to a pulling force in the approximate range 105N to 135N. The skilled person will also appreciate that the dimensions of the inner member 24 and outer casing 26 will also determine the predetermined force at which the disabling device decouples. In the present embodiment, the component parts are selected and dimensioned so that decoupling occurs at a pulling force of approximately 135N.

The helical rib 60 extends around approximately 340 degrees about the circumference of the barrel 52 such that the driving member 62 can only drive the rib 60 to rotate the barrel when the handle casing 24 is sliding away from the blade end of the forceps. On the return stroke caused by spring 42 when the pulling force is removed, the driving member does not drive against helical rib 60 and so barrel 52 does not rotate and so records the maximum amount of pulling force applied. If the helical rib 60 passed through more than 360 degrees, then driving member 62 would also be able to drive helical rib 60 on the return path when the force is released and thereby turn the helical rib 60 in the opposite direction.

Figure 9:
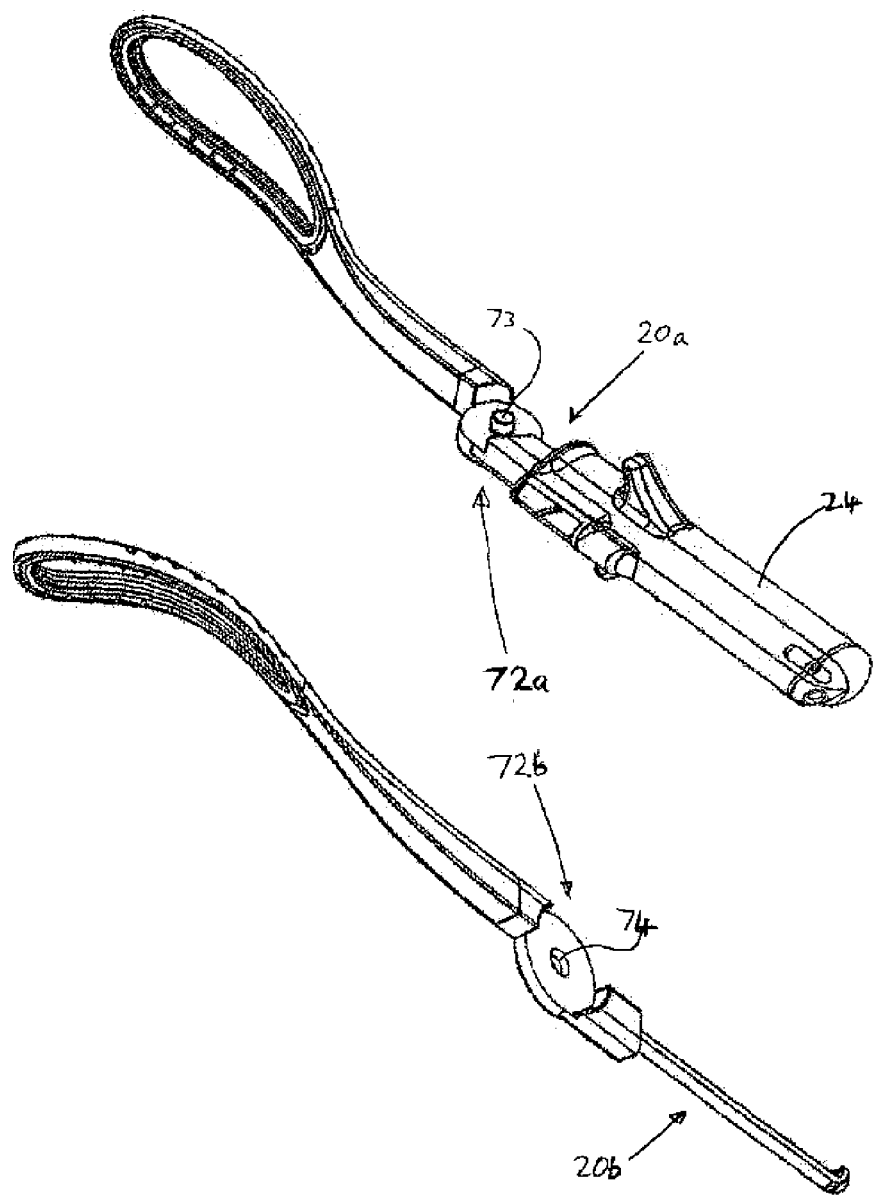
FIG. 9 shows the two parts of the forceps of FIG. 1 separated before assembly for use.
Figure 10:
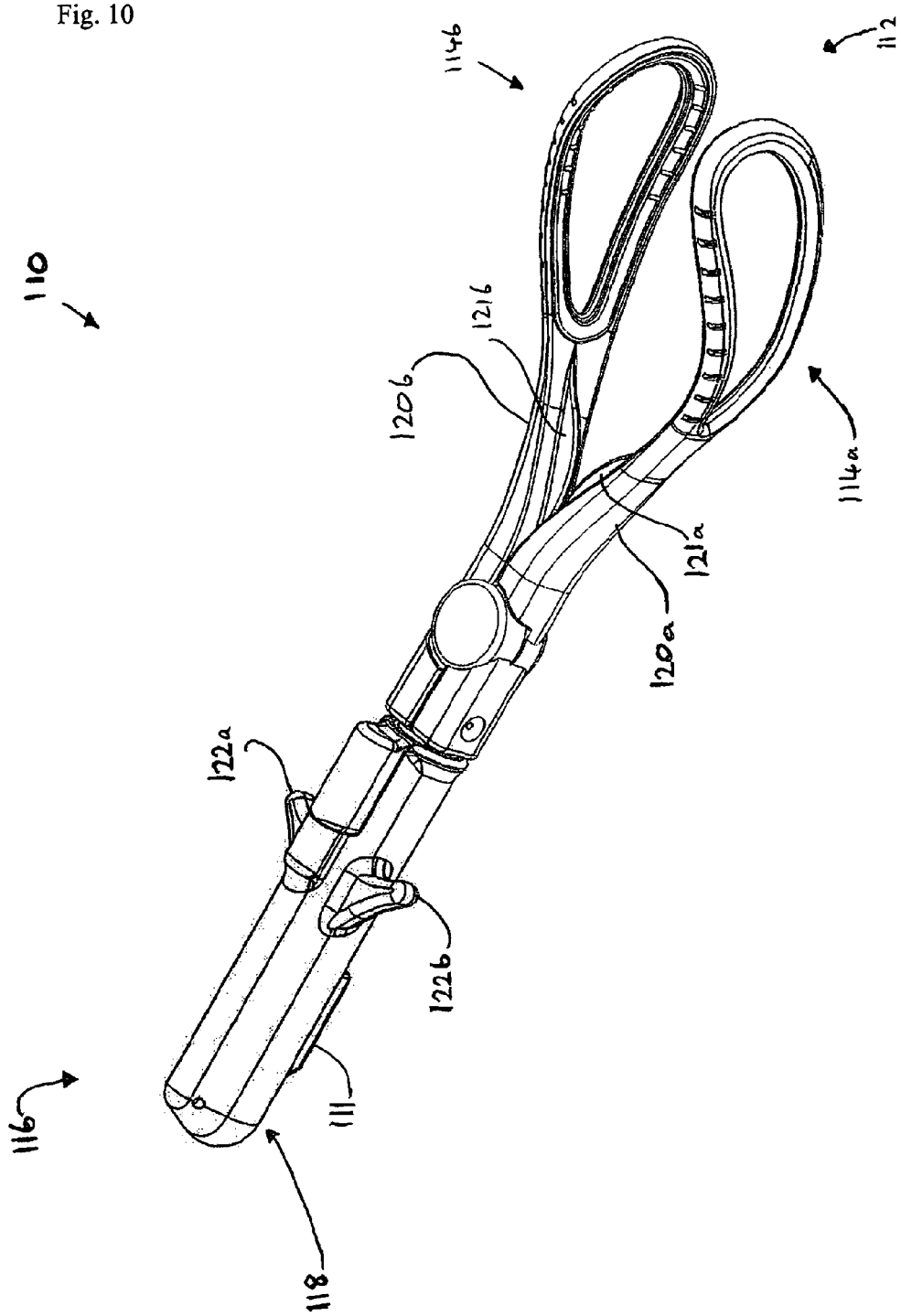
FIG. 10 shows a perspective view of a further pair of obstetric forceps according to the present invention.

The first and second shanks 20a, 20b each include respective parts of 72a, 72b a two part rotational bearing 72 (as best illustrated in FIG. 9) such that when the two parts are coupled together the shanks 20a 20b are fixed in a scissor-like arrangement. The two-part rotational bearing 72 is in the form of a pin 73 and matching socket 74 coupling in which the first shank 20a includes a pin which is mateably received in the socket located in the bearing part 72 of the second shank 20b.

Figure 4:
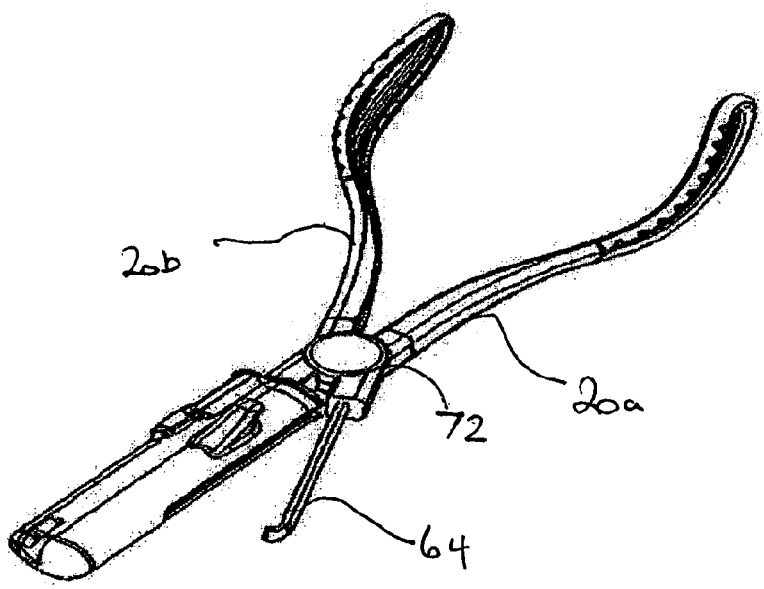
FIG. 4 shows the obstetric forceps of FIG. 1 prior to the blades being locked in place.

FIG. 4 shows the handle 18 of the forceps 10 positioned ready to receive the free end 64 of the second shank 20b into the locking mechanism. The locking mechanism includes the elongate channel 66 in the anchor member 48 (which receives and retains the free end 64), the outer casing 24 and inner member 26.

As can be seen from FIG. 2, the elongate channel 66 runs parallel to the longitudinal axis of the anchor member 48 and extends approximately three quarters of the length of the anchor member 48. The elongate channel 66 terminates with a perpendicular portion 68 which extends into the anchor member 48 toward the longitudinal axis. The free end 64 is dimensioned so as to be snugly received within the elongate channel 66 of the anchor member 48 with a hooked end 70 formed at 90 degrees to the longitudinal axis of the second shank 20b so as to be received within the perpendicular portion 68 of the elongate channel. Hence, once the free end 64 is received within the channel 66, movement of the second shank 20b along the longitudinal axis is prevented due to the mating faces of the hooked end 70 and the perpendicular face portion 68 of the channel 66.

The inner member 26 and outer casing 24 include corresponding longitudinal apertures 74, 76 which extend from their respective ends. When the inner member 26 is received within the outer casing 24 and the apertures 74, 76 are rotationally aligned relative to the elongate channel 66 of the anchor member 48 as shown in FIG. 4, there is provided an opening through which the free end 64 of the second shank 20b can pass into the elongate channel 66. Once received within the elongate channel 66, the locking mechanism is operated by rotating the outer casing 24 and inner member 26 through approximately 90 degrees in a clockwise direction on the threaded portion 50 so as to capture the free end 64 by the action of the wall of the inner member 26. Thus, the locking mechanism provides the obstetric forceps 10 with a shank attachment which ensures that the blades 14a, 14b are firmly attached to the handle 18 relative to one another and that the outer casing 24 is still free to slide along the inner member 26.

Further, the outer casing shields the free end 64 of shank 20b from external compressive forces which would otherwise cause the forceps blades to close more and therefore prevents any further compressive force being applied by the forceps blades. That is, the locking member also acts to lock the forceps blades at a fixed separation.

Figure 6:
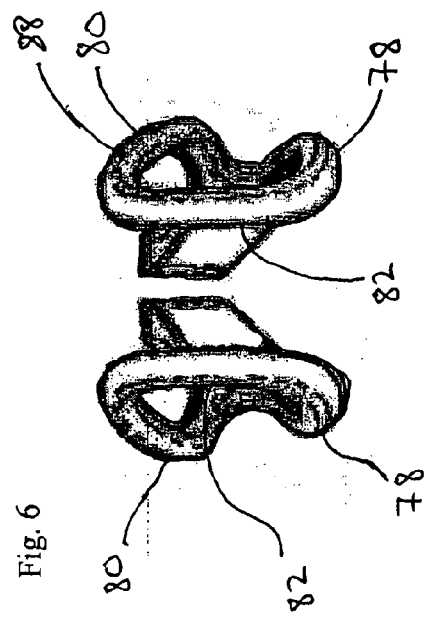
FIG. 6 shows an end view of the obstetric forceps blades.
Figure 7:
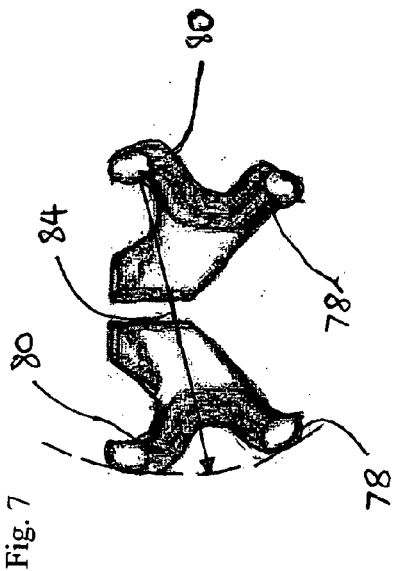
FIG. 7 shows a cross section of the obstetric forceps blades along line C-C as shown in FIG. 5.
Figure 5:
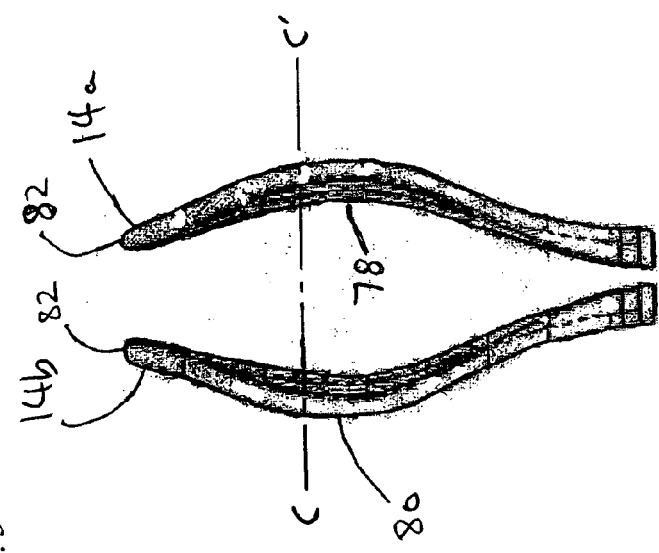
FIG. 5 shows a plan view of the obstetric forceps blades.

FIGS. 5, 6 and 7 show the configuration of the first and second blades. The first and second blades 14a, 14b are fenestrated, each having an inferior rim 78, a superior rim 80 and an end rim 82 which connect to form a loop. When viewed from above, as shown in FIG. 5, the opposing superior 80 and inferior 78 rims of the blades 14a, 14b are curved so as to define an approximate oval shape between corresponding rims. The distance between corresponding parts of the inferior rims 78 is less than between corresponding parts of the superior rims 80 so that the oval shape formed by the curvature of the inferior rims 78 is smaller than that created by the superior rims 80. In this way the contours defined by the cephalic side of the blades 14a, 14b is bowl shaped. The bowl like shape or configuration of the blades can also be seen in the end view of FIG. 6 in which it can be seen that the blades taper inward and toward each other as you move in a superior to inferior direction and so are shaped like a bowl to cup around the baby's head in use.

As can also be seen in FIG. 6 (and also FIG. 7), the vaginal wall engaging edges of the forceps blades have a smooth continuous surface and so do not present any kind of edge or other discontinuity which may act to cut or otherwise damage the vaginal wall in use.

The pelvic side of the superior 80 and inferior 78 rims include surfaces which contact the vaginal wall in use. The contours which lie in a given cross-sectional plane of the contacting surfaces define an arc having a fixed radius 84 with an origin approximately located on the opposing superior rim (as shown by the dashed line in FIG. 6 for the rims of the first blade 14a). Hence, the contacting surfaces of the superior 80 and inferior 78 rims collectively define or lie on portions of a smooth curved surface which is substantially bowl shaped.

The curvature defined by the inferior rims 78 and superior rims 80 redistributes the stress away from the lateral margins of the vaginal fourchette during use, thereby reducing the risk of perineal damage.

The curvature of the inferior and superior rims also presents a smooth surface to the vaginal walls in use, rather than an edge. This helps prevents an edge, or other discontinuity in the surface of the blades, from imparting a cutting type action on the vaginal walls and hence reduces the chance of harm.

Figure 8:
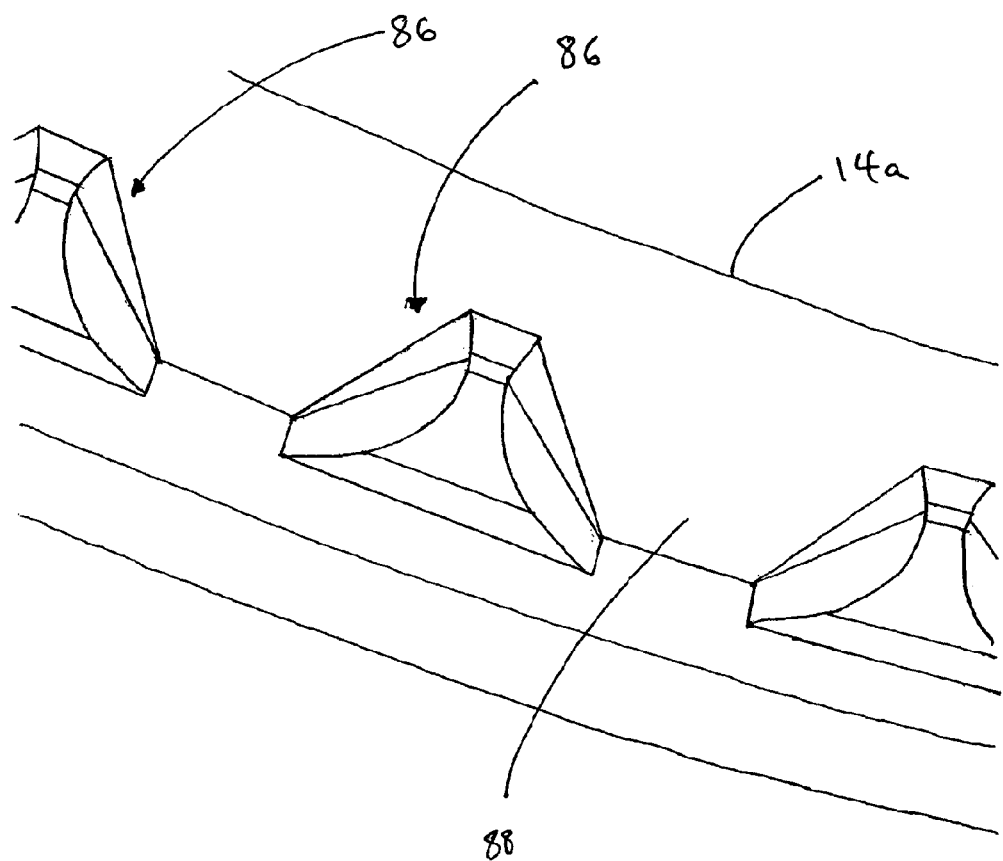
FIG. 8 shows a pelvic side view of a superior rim of the forceps.

FIG. 8 shows a close up of a feature present in the pelvic side of the inferior 78 and superior 80 rims. Both the inferior and superior rims include recessed portions 86 as also shown in FIG. 1. The recessed portions 86 are in the form of approximately triangular cavities in the contacting surface of the rims. In use, the perineum stretches over the recessed portions 86 such that the surface contact between the perineum and the pelvic side of the blades 14a, 14b is reduced. This helps reduce the friction and any resulting perineal damage.

The cephalic side of the rims 78, 80 include a portion made from a soft polymer material 90 having raised portions 92 which help increase grip on the baby's face and head whilst helping to reduce frictional related tearing of the skin.

In the present embodiment, the handle, shanks and blade frames are made from a glass reinforced plastic material so as to be manufactured inexpensively and therefore disposable after a single use. This has the advantage that no sterilization of the forceps 10 is required and each delivery room in a hospital suite or individual emergency response vehicle can be equipped with a pair of the obstetric forceps.

It will be apparent that other materials having the suitable mechanical and medical properties can be used. For example, non-disposable forceps can be made from metals and alloys such as surgical grade stainless steel.

To assemble the obstetric forceps, the spring 42 and female coupling part 38 are attached together and the female coupling part 38 is mated with the male coupling part 34. The inner member 26 is slotted part way into the outer casing 24 along axis 25 such that the channel 44 on the upper side of the outer casing 24 receives the female coupling portion 36 and spring 42, and the ribs 32 on the inner member 26 are received with the corresponding formations on the inner surface of the outer casing 24. The distal end of the spring 42 is then attached to the cap 30 before the inner member 26 is pushed completely into the outer casing 24 so as to allow the cap 30 to be attached to the outer casing.

The anchor member 48 having the first shank 20a already attached is screwed all the way into inner member 24 on the threaded portion 50. Once screwed home, the anchor member 24 is screwed back a quarter of one turn to align the inner member aperture 74 and outer casing aperture 76 with the elongate channel 66 in the anchor member 48 as shown in FIG. 4. The first and second blades 14a, 14b are then positioned next to the baby's head in the birth canal at the appropriate position for gripping and applying the pulling force for delivery. Once correctly positioned, the shanks 20a, 20b are gently brought together and the pin 73 and socket 74 of bearing 72 are mated. Mating the pin and socket bearing 72 fixes the blades 14a, 14b in mutually opposing positions and allows the free end 64 of the second shank 20b pivot about bearing 72 so as to be received by the elongate channel 66 via the apertures 74, 76 in the outer casing 24 and inner member 26. Once the free end 64 of the second shank 20b is received within the anchor member channel 66, the outer casing 24 and inner member 26 are screwed a quarter of a turn in a clockwise direction so as to position the apertures 74, 76 on the underside of the handle as shown in FIG. 1. The rotation of the handle 18 in this way retains the free end in the anchor member 48 with the wall of the inner member 24 and locks the blades in position.

The user positions their hand above the handle 18 from the proximal end 16 and curls a fore finger and index finger over respective finger grips 22. The shaft of the handle 18 is received within the palm of the user's hand. Once a firm grip has been taken, a pulling force can be exerted on the baby's head via the blades 14a, 14b. As the force increases, the outer casing 24 slides relative to the inner member 26 and the driving member 62 enters the force indicator housing 54 through the notch 63 in the housing wall 65. The driving member 62 engages the helical rib 60 on the barrel 52 and causes the barrel to rotate as the force increases thereby displaying each coloured portion in turn to the user through the window portion 56. This provides the user with a visual indication of the force which is currently being applied.

If the force passes the predetermined maximum amount limit, then the two part coupling enters the chamber 46 where the female coupling part 36 is no longer restrained by the roof of channel 44 and rises up under the tensile force of the spring 42 and the male 34 and female 36 parts become disconnected. The female coupling part then freely retracts under the force of the spring 42 into the channel 44.

The removal of the biasing force of the spring 42 results in the outer casing 24 being able to slide freely over the inner member 26 until the male coupling part 34 contacts the wall 65 of the force indicator housing 54 which acts as a restraint. The notch is sized to prevent the male coupling part 34 passing through, thereby stopping the relative motion between the outer casing 24 and the inner member 26.

The small but sudden acceleration due to the disconnection of the spring 42, and the deceleration as the male coupling part 34 hits the distal wall 65, as well as the removal of the biasing force, provides the user with instant tactile feedback that the maximum force has been reached and that the pulling force should be removed. The contacting of the male coupling part 34 on the distal wall 65 also provides an audible indication to others present during the assisted delivery that the maximum safe force has been reached.

Once the spring 42 has disconnected and the force removed, the relative movement between the outer casing and inner member 26 is no longer biased and the outer casing 24 is free to slide along the inner member 26 unhindered. Hence, if the pulling force is removed and then reapplied, the person reapplying the pulling force will know that the maximum force has been reached as the handle part of the forceps has become disabled, i.e. does not work as it did prior to exceeding the maximum force limit. Hence, the normal operation of the forceps has been partially disabled.

If the spring 42 has not disconnected prior to the baby being delivered, the outer casing 24 and inner member 26 will be returned to the original resting position when the pulling force is removed. When this occurs, the driving member 62 passes back out of the force indicator housing 54 via the notch 63 into the chamber 46. Because the rotation of the barrel 52 is restricted to be less than 360 degrees, the driving member 62 passes back into the chamber 46 without driving the helical rib 60 on its return. Hence, counter rotation of the barrel 52 is prevented and the maximum pulling force which has been applied is recorded and can be read. The force used can then be recorded in the mother and baby's medical records for future use.

The two parts of the obstetric forceps can be disassembled by rotating the handle 18 and removing the free end 64 from the anchor member 48 and decoupling the pin and socket bearing 72 before separating the two parts.

FIGS. 10 to 13 show a second embodiment of a pair of obstetric forceps 110 also according to the invention. The construction of the second embodiment is substantially similar to the first embodiment, but with some structural differences.

The obstetric forceps 110 have first and second blades 114a, 114b toward a first or distal end 112 and a handle 118 toward second or proximal end 116. The first and second blades 114a, 114b are connected to the handle 118 via respective first 120a and second 120b shanks. First and second finger grips 122a, 122b extend from opposite sides of the handle 118 such that a user of the obstetric forceps 110 can hook their fingers over the finger grips to help exert a pulling force on the head of a baby.

Each shank 120a, 120b includes a reinforcing member in the form of a curved rib 121a, 121b which extends outwardly from a respective inner surface of each shank into a gap between the shanks. The reinforcing members act to increase the strength of the forceps, particularly their rigidity in the direction of the plane in which the ribs lie, and in a direction generally transverse to the longitudinal axis of the forceps and perpendicular to the plane of the blades. This increased stiffness of the shanks allows an increased compressive force to be applied without bending the forceps.

Figure 11:
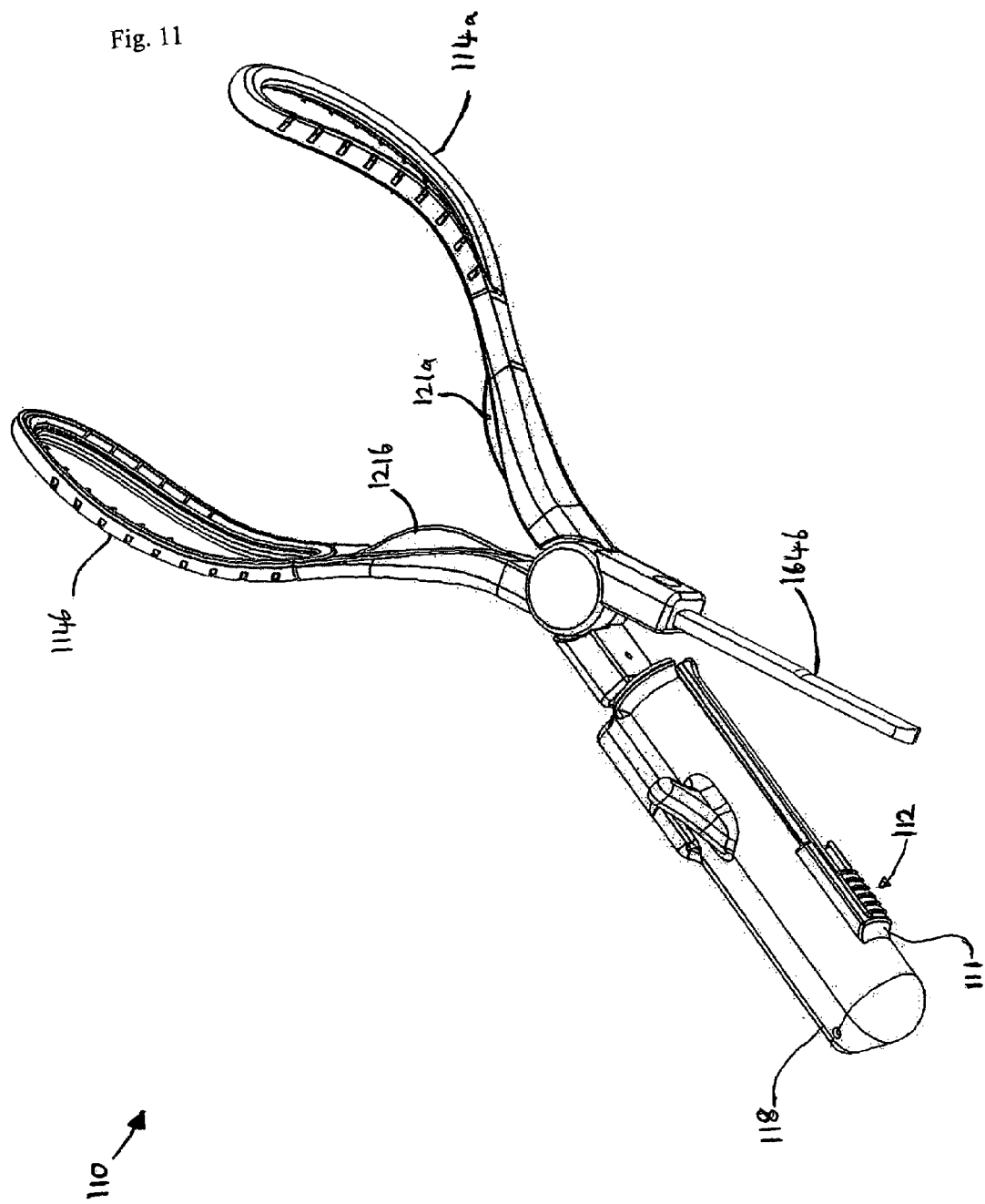
FIG. 11 shows a perspective view of the pair of obstetric forceps of FIG. 10 in an open configuration.
Figure 12:
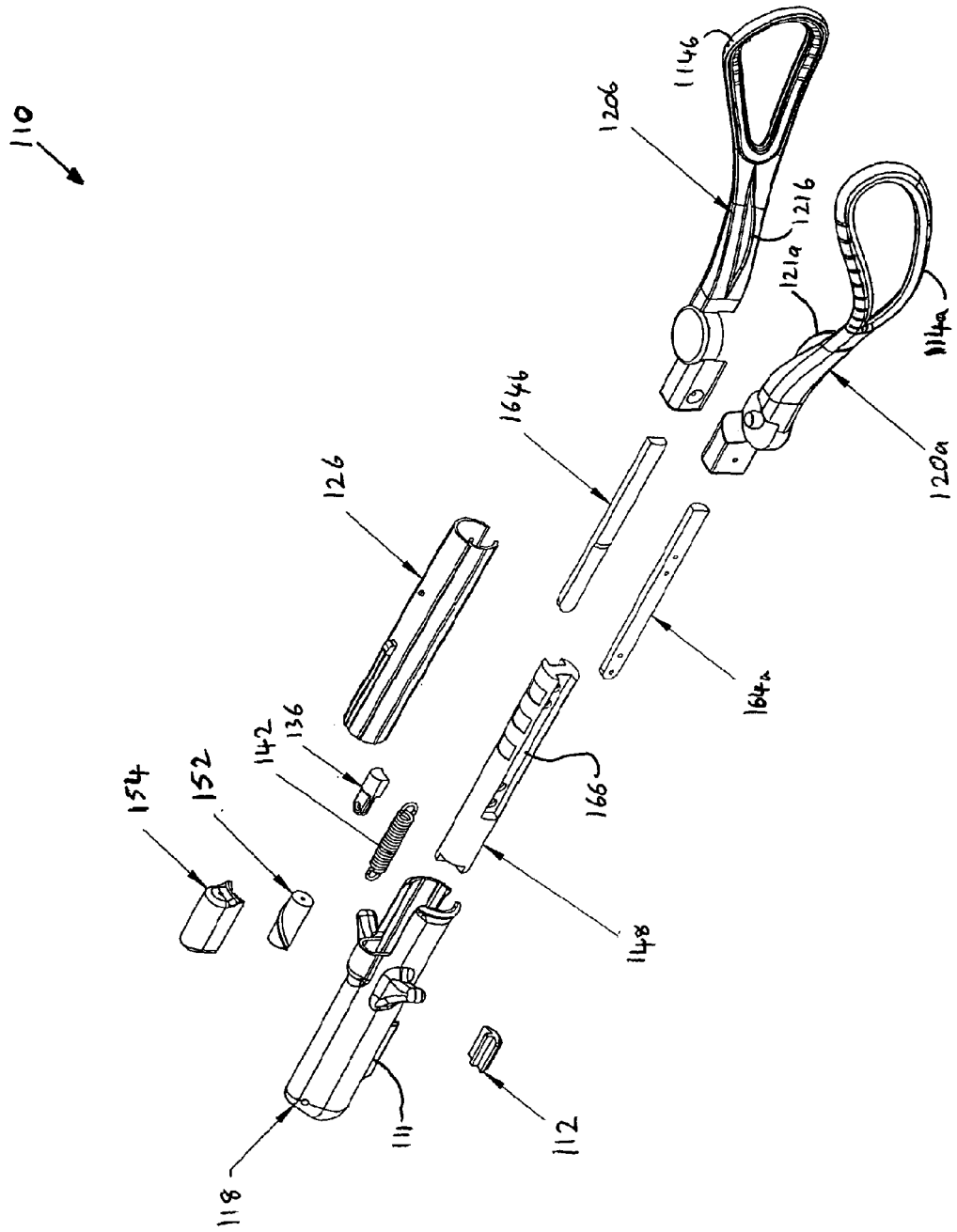
FIG. 12 shows an exploded view of the pair of obstetric forceps of FIGS. 10 and 11.
Figure 13:
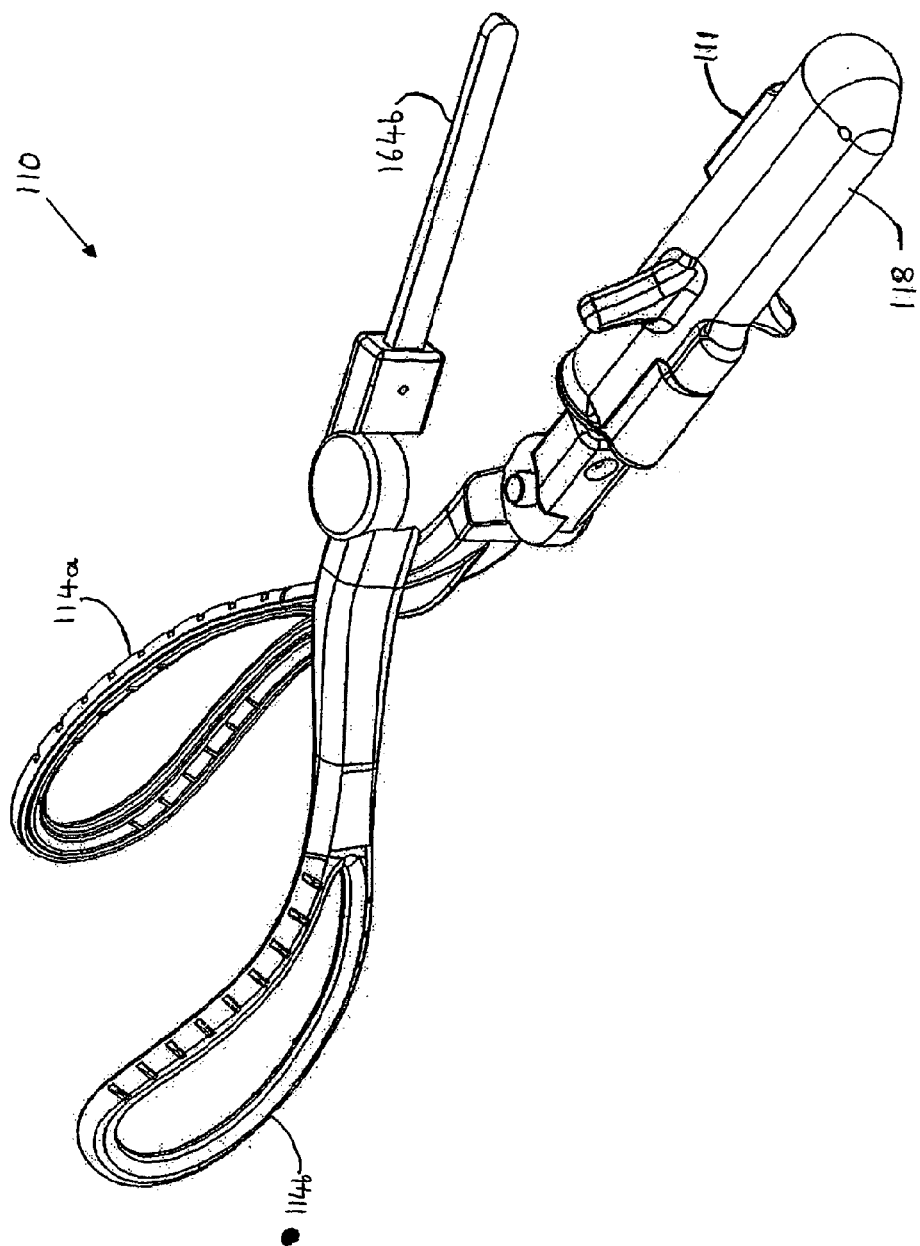
FIG. 13 shows a perspective view of the pair of obstetric forceps of FIGS. 10 to 12 in a separated state.

As best illustrated in FIGS. 11 and 12, an underside or bottom surface of the handle 118 includes a housing 111 in which a catch 112 is slidably retained so that the catch can be slid along the direction of the longitudinal axis of the forceps.

The catch has a curved body with a rib extending therefrom and a plurality of ridges on an exposed surface providing enhanced grip to a user. Catch 112 can be slid in a distal direction in order to retain arm 164 within channel 166 of the anchor member 148.

The mechanically operating disabling device as illustrated in FIG. 12 is similar to that described above for the first embodiment. A detachable coupling links the outer casing part of the handle 118 to the remainder of the forceps. A resilient element in the form of a spring 142 provides a biasing force. Indicator barrel 152 sits within indicator housing 154 and is driven to rotate therein. Coupling part 136 includes a flat tongue extending from its body and having an aperture for receiving a hook at one end of spring 142. The disabling device operates on the same principles to those of the disabling device of the first embodiment.

Various parts of the forceps can include apertures or openings providing access to fixings for attaching the parts of the forceps together so as to facilitate their assembly.

It will be appreciated that the mechanical force indicator and disabling device can be used in a pair of obstetric forceps which do not include the bowl-like blades described above. It will also be appreciated that the bowl-like blades will have application in any obstetric forceps and not only those including a mechanical force indicator and disabling device.

It will also be appreciated that the visual indication provided by the coloured portions could be replaced with any other suitable visual indicator such as a sliding scale. Further, having greater or fewer than three colours is possible.

The ranges of forces described above for each coloured portion is provided as an example only. The actual safe operational pulling forces may differ depending on the circumstances.

The invention claimed is:

1. A pair of obstetric forceps, comprising:
   a pair of blades at a first end for holding the head of a baby;
   a handle at a second end having at least one part by which a user can apply a pulling force on the head of the baby in use;
   a mechanically operated force indicator connected to the at least one part of the handle and operable to provide a visual indication of the amount of pulling force being applied to the head of the baby when a user applies a pulling force on the head of the baby in use, and wherein the force indicator is responsive to an increase only in the pulling force, and the force indicator automatically records the maximum pulling force applied; and
   a mechanically operated disabling device operable to at least partially disable the obstetric forceps when a maximum pulling force has been exceeded.

2. A pair of obstetric forceps as claimed in claim 1 wherein the disabling device at least partially disables the at least one part when the maximum force is exceeded.

3. A pair of obstetric forceps as claimed in claim 2, wherein the disabling device at least partially disables the entire handle when the maximum force is exceeded.

4. A pair of obstetric forceps as claimed in claim 1, wherein the disabling device includes a detachable coupling between the at least one part and the blades and wherein the detachable coupling detaches when the maximum force is exceeded.

5. A pair of obstetric forceps as claimed in claim 4, wherein the detachable coupling includes a resilient member which resiliently biases the at least one part in a first position relative to the blades and wherein when the detachable coupling detaches the at least one part is no longer biased toward the first position.

6. A pair of obstetric forceps as claimed in claim 1, further comprising a restraint which prevents the part and the blades becoming entirely separated when the obstetric forceps become at least partially disabled.

7. A pair of obstetric forceps as claimed in claim 1, wherein the force indicator includes a plurality of visual indicia, each corresponding to a range of applied pulling force.

8. A pair of obstetric forceps as claimed in claim 1, and wherein the obstetric forceps comprises two parts, each part having a shank part attached to a respective blade.

9. A pair of obstetric forceps as claimed in claim 8, wherein the shanks are pivotably connectable to each other by a releasable pivot mechanism to form a scissors-like construction.

10. A pair of obstetric forceps as claimed in claim 8, wherein a first of the shanks can be releasably fastened to the handle by a locking mechanism.

11. A pair of obstetric forceps as claimed in claim 10 wherein the locking mechanism is operable by rotating a part of the handle so as to capture at least a portion of the first shank.

12. A pair of obstetric forceps as claimed in claim 1, and further including at least one reinforcing member located proximally of the blades and configured to increase the stiffness of the forceps.

13. A pair of obstetric forceps as claimed in claim 1, wherein the force indicator automatically provides a visual indication of the maximum pulling force applied after the pulling force is removed.

14. A pair of obstetric forceps as claimed in claim 1, wherein when the obstetric forceps is at least partially disabled by the disabling device, the handle no longer operates in the same way in allowing the pulling force to be exerted on the head of the baby as compared to when the obstetric forceps is not at least partially disabled by the disabling device.

15. A pair of obstetric forceps as claimed in claim 1, wherein when the disabling device at least partially disables the obstetric forceps, the at least one part of the handle slides freely relative to the remainder of the forceps.

* * * * *